(12) United States Patent
Stern et al.

(10) Patent No.: US 6,444,441 B1
(45) Date of Patent: *Sep. 3, 2002

(54) PRODUCTION OF HUMAN MUTATED PROTEINS IN HUMAN CELLS BY MEANS OF HOMOLOGOUS RECOMBINATION

(75) Inventors: Anne Stern; Konrad Honold, both of Penzberg (DE)

(73) Assignee: Roche Diagnostics GmbH, Mannheim (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/463,338

(22) PCT Filed: Jul. 22, 1998

(86) PCT No.: PCT/EP98/04583

§ 371 (c)(1),
(2), (4) Date: Jan. 21, 2000

(87) PCT Pub. No.: WO99/05264

PCT Pub. Date: Feb. 4, 1999

(30) Foreign Application Priority Data

Jul. 23, 1997 (EP) .............................. 97112639

(51) Int. Cl.⁷ ..................... C12N 15/09; C12N 15/87; C12N 5/00; C12P 21/02; C07H 21/04
(52) U.S. Cl. ................... 435/69.1; 435/69.7; 435/325; 435/440; 435/455; 435/463; 435/464; 536/23.1; 536/23.4
(58) Field of Search ................. 435/69.1, 440, 435/455, 464, 69.7, 463, 325

(56) References Cited

U.S. PATENT DOCUMENTS 5,234,686 A * 8/1993 Dodd ..................... 424/94.64
6,270,989 B1 * 8/2001 Treco et al. ............... 435/69.1

FOREIGN PATENT DOCUMENTS

| EP | 0382174 | 8/1990 |
| WO | 9203917 | 3/1992 |
| WO | 9220808 | 11/1992 |
| WO | 9531560 | 11/1995 |

OTHER PUBLICATIONS

O. Smithies et al., *Nature*, 317:230–234 (Sep. 19, 1985).
S.L. Mansour et al., *Nature*, 336:348–352 (Nov. 24, 1988).
K.R. Thomas et al., *Cell*, 51:503–512 (Nov. 6, 1987).
P. Hasty et al., *Molecular and Cellular Biology*, 11:11:5586–5591 (Nov. 1991).
M.R. Capecchi et al., *Science*, 244:1288–1292 (Jun. 16, 1989).
R.J. Bollag et al., *Annu. Rev. Genet.*, 23:199–225 (1989).
R.S. Kucherlapati, *Process in Nucleic Acid Research and Molecular Biology*, 36:301–310 (1989).

* cited by examiner

*Primary Examiner*—David Guzo
*Assistant Examiner*—Gerald G. Leffers, Jr.
(74) *Attorney, Agent, or Firm*—Fulbright & Jaworski, LLP

(57) ABSTRACT

The invention concerns a process for the production of muteins of eukaryotic polypeptides in eukaryotic cells by means of homologous recombination. The invention additionally concerns a process for the production of human cells which are suitable for the production of human mutated proteins. Finally the invention concerns the human cells produced by the process and mutated human proteins obtainable therefrom as well as pharmaceutical preparations which contain these muteins.

18 Claims, No Drawings

PRODUCTION OF HUMAN MUTATED PROTEINS IN HUMAN CELLS BY MEANS OF HOMOLOGOUS RECOMBINATION

DESCRIPTION

The invention concerns a process for the production of muteins of eukaryotic polypeptides in eukaryotic cells by means of homologous recombination. The invention additionally concerns a process for the production of human cells which are suitable for the production of human mutated proteins. Finally the invention concerns the human cells produced by the process and mutated human proteins obtainable therefrom as well as pharmaceutical preparations which contain these muteins.

The production of recombinant human proteins in large amounts is known in the field of biotechnology. Proteins obtained in this manner can be used as therapeutic agents. The recombinant production of mutated human proteins which differ from corresponding natural human proteins by deletion, addition or/and substitution of individual amino acids or whole peptide sections is also known.

Especially for pharmaceutical applications it is often desirable to produce human polypeptides in eukaryotic cells since, in contrast to polypeptides produced in prokaryotic cells such as E. coli, these are glycosylated and therefore differ less from the polypeptides that occur endogenously in the body so that the occurrence of undesired side effects such as for example increased immunogenicity or poor tolerance is less frequently observed.

Mutated human proteins have been previously produced by heterologous recombinant gene expression. For this a nucleic acid construct is introduced into the desired eukaryotic cell which contains the nucleic acid sequence coding for the mutated polypeptide under the control of a promoter and a selection marker gene. In this process the nucleic acid construct is integrated site-unspecifically into the genome of the cell.

In this heterologous recombinant gene expression undesired and disadvantageous processes can frequently occur due to the site-unspecific integration. For example mutations and especially deletions in the sequence coding for the protein can occur during the process of integration into the genome. Furthermore the integration can take place at a site in the genome at which Cis elements are located which have a repressing effect on the expression control sequence of the nucleic acid construct and as a result of which cells are obtained with a reduced production output for the recombinant protein. An integration of the expression construct into an important gene for the cell leads either to death of this cell or to a recombinant cell with functional disorders which can, among others, result in a reduced yield of the recombinant protein.

The insertion can also lead to a reduced stability of the cells obtained in this manner so that over a long period they lose their ability to express the recombinant protein.

The object of the present invention was therefore to provide a process for the production of muteins of eukaryotic polypeptides with a glycosylation which is as similar as possible to that of the natural protein, in a stable production cell and in good yields and thus at least partially eliminate the disadvantages of the prior art.

This object is achieved according to the invention by a process for the production of muteins of eukaryotic polypeptides wherein (i) a nucleic acid molecule capable of homologous recombination is introduced into eukaryotic cells which contain a target nucleic acid sequence coding for an endogenous target polypeptide, the said nucleic acid molecule comprising (a) at least one sequence section which is homologous to sequences in the gene locus of the target nucleic acid sequence and, compared to the endogenous target nucleic acid sequence, has a mutation in the coding region of the mature polypeptide and (b) a nucleic acid section coding for a selection marker, (ii) the cells are cultured under such conditions that a homologous recombination of the introduced nucleic acid molecule takes place whereby the cell contains a mutated target nucleic acid sequence after the homologous recombination which is able to express a mutein of the target polypeptide, (iii) the cells, in which a homologous recombination has taken place, are selected and (iv) the mutein is isolated from the cells or/and the cell supernatant.

Mutated eukaryotic proteins and in particular mutated human proteins can be produced in a homologous cell by the process according to the invention. surprisingly this enables a mutated protein to be obtained in high yields with a very similar glycosylation pattern to that of the natural protein. An advantage of the process according to the invention is that a protein can be mutated in a eukaryotic cell and this mutein is synthesized by this cell like the protein of the cell that occurs endogenously. A further advantage of the process according to the invention is that the properties of the resulting cells that produce the mutated protein are not disadvantageously altered due to a site-unspecific gene integration. Thus the genome of the cell is not changed in any manner apart from the gene locus of the protein to be expressed and hence the associated adverse effects can be excluded.

The human mutated protein produced by the process according to the invention differs from the corresponding natural protein by deletion, addition or/and substitution of individual amino acids or whole peptide sections. Muteins are preferably produced which have mutations at the N-terminus and/or at the C-terminus such as e.g. deletions, insertions, substitutions or/and fusions with other e.g. human proteins.

The muteins according to the invention are preferably non-naturally occurring polypeptides and differ from allelic variations of the polypeptide to be mutated which occur naturally in other starting cells by at least one amino acid. Non-naturally occurring muteins particularly preferably differ by deletions, additions or/and insertions of individual amino acids or peptide sections from naturally occurring allelic variations.

The cell used in the process according to the invention is an arbitrary eukaryotic cell which has at least one endogenous copy of the target gene to be mutated. The cell is preferably a human cell, particularly preferably an immortalized human cell such as a HeLa cell, a Namalwa cell or a HT1080 cell.

It was surprisingly found that when starting cells are used which contain an increased number of chromosomes on which the target gene is located, cells can be produced by homologous recombination which produce an increased yield of mutated human proteins compared with cells which only contain two copies of the target gene. Examples of such starting cells are tumour cell lines with genetic rearrangements such as HeLaS3 (Puck et al., J.Exp.Med. 103 (1996), 273–284) and Namalwa (Nadkarni et al., Cancer 23 (1969), 64–79) which contain an increased number of copies of the chromosome 7.

An endogenous gene activation of the mutated target gene can be carried out to further improve the expression of the mutated polypeptide.

For this additional sequences can be introduced into the genome which positively influence the expression yield in which for example the endogenous expression control sequence of the target nucleic acid sequence is replaced at least partially by a heterologous expression control sequence. This heterologous expression control sequence can contain a heterologous promoter or/and enhancer, the heterologous expression control sequence preferably contains a viral promoter, in particular a CMV promoter. Replacement of the endogenous promoter not only enables the expression to be increased but allows synthesis of the mutein when a suitable promoter is used. The heterologous promoter can be a regulatable or constructive promoter. In addition this can be used to inactivate Cis elements that have a repressive effect on the endogenous promoter. This can also lead to an increase in yield.

The nucleic acid molecule introduced into the starting cell comprises at least one sequence section which allows an integration by homologous recombination in the locus of the target gene and is suitable for introducing the mutation in the coding region of the mature target polypeptide. The nucleic acid molecule preferably contains two flanking sequences which are homologous to regions of the target gene locus. The flanking sequences preferably each have a length of at least 150 bp and contain regions from the sequences of the target gene locus coding for the mature target polypeptide which are modified compared to the native sequence.

In addition the nucleic acid molecule contains a selection marker gene. This can be any suitable selection marker gene for eukaryotic cells which leads to a selectable phenotype on expression e.g. antibiotic resistance, auxotrophy, expression of a surface protein etc. The neomycin phosphotransferase gene is a particularly preferred selection marker gene.

In addition the nucleic acid molecule can optionally contain a negative selection marker gene e.g. a HSV thymidine kinase gene whose expression destroys cells in the presence of a selective agent.

If an amplification of the modified target gene in the cell is desired, the nucleic acid molecule contains an amplification gene. Examples of suitable amplification genes are dihydrofolate reductase, adenosine deaminase, ornithine decarboxylase etc. The dihydrofolate reductase gene is a particularly preferred amplification gene.

When the amplification gene is present, the mutated target nucleic acid sequence can be amplified after the homologous recombination in order to increase the number of copies in the cell.

The process according to the invention enables the mutation of all endogenous genes present in the genome of the cell used. The target nucleic acid sequence is preferably a tissue plasminogen activator (tPA), erythropoietin, insulin, tumour necrosis factor, interleukin or interleukin receptor sequence. The mutein obtained by the process according to the invention is particularly preferably a polypeptide whose biological properties differ from those of the corresponding natural protein, such as a polypeptide derived from t-PA comprising the K2 and P domains of t-PA (EP 0 382 174).

The known techniques can be used to isolate the mutein. The mutein is preferably isolated from the supernatant of cells cultured in suspension. Cells that can be cultured in suspension are especially advantageous for a large-scale production. This considerably simplifies the transfers of cultured cells that are necessary during the course of the production process. This leads to a considerable saving of production time and production resources and hence significantly reduces costs. The mutein is particularly preferably isolated from the supernatant of cells cultured in serum-free medium. The mutein can be isolated more simply and cheaply from cells cultured in serum-free medium in contrast to cells cultured with serum since fewer purification steps are necessary.

A further subject matter of the present invention is a mutated human polypeptide from a human cell obtainable by one of the processes described above which is distinguished by human glycosylation and the absence of polypeptides that are foreign to the species. The absence of polypeptides that are foreign to the species means less than 3% by weight impurities of polypeptides foreign to the species, preferably less than 1% by weight and most preferably less than 0.1% by weight relative to the amount of the desired protein.

A further subject matter of the invention is a process for the production of a human cell which expresses a mutein of a human target polypeptide which is characterized in that (i) a nucleic acid molecule is introduced into human cells which contain a target nucleic acid sequence coding for an endogenous target polypeptide, the said nucleic acid molecule comprising
   (a) at least one sequence section which is homologous to sequences in the gene locus of the target nucleic acid sequence and, compared to the endogenous target nucleic acid sequence, has a mutation in the coding region of the mature target polypeptide,
   (b) optionally a heterologous expression control sequence for the target nucleic acid sequence and
   (c) a nucleic acid section coding for a selection marker,
(ii) the cells are cultured under such conditions that a homologous recombination of the introduced nucleic acid molecule takes place whereby the cell contains a mutated target nucleic acid sequence after the homologous recombination which is able to express a mutein of the target polypeptide,
(iii) the cells, in which a homologous recombination has taken place, are selected and
(iv) the cells selected in this way are isolated.

In a preferred embodiment the nucleic acid molecule additionally contains an amplification gene and the mutated target nucleic acid sequence is amplified after the homologous recombination.

A further subject matter of the invention is a human cell obtainable by a process as described above which contains at least one endogenous gene coding for a mutated human polypeptide.

The cell according to the invention can be cultured under suitable culture conditions and it is preferably a cell that grows in suspension and particularly preferably a cell that grows in serum-free medium.

A further subject matter of the invention is the use of a human cell produced by a process as described above for the production of a mutein of a human polypeptide.

Yet a further subject matter of the invention is a pharmaceutical preparation which is characterized in that it contains a mutein as described above as the active substance optionally together with other active substances or/and common pharmaceutical carriers, auxiliary substances or additives.

EXAMPLE

Construction of a t-PA mutant which contains the K2 and P domains:

a) Vector Construction

The targeting vector is composed of the following elements (listed in the 5'-3' sequence):

A: a 6 kb BgIII fragment which contains about 3.5 kb of the 5' upstream region of the t-PA gene (Friezner et al. 1986, JBC 261 (15): 6972)

B: an approximately 5.2 gene activation sequence (as an AgeI fragment) which contains the neomycin phosphotransferase (NEO) gene under the control of the RSV promoter and the late polyadenylation site of SV40 as the terminator, a gene coding for an arginine mutant of the murine dihydrofolate reductase (DHFR) (Simonsen et al., Proc. Natl. Acad. Sci. USA 80 (1983), 2495) under the control of the early SV40 promoter and the early SV40 polyadenylation site as the terminator (Kaufmann et al., Mol. Cell. Biol. 2 (1982), 1304; Okayama et al., Mol. Cell. Biol. 3 (1983), 280 and Schimke, J. Biol. Chem. 263 (1988), 5989) and the cytomegalo-virus (CMV) promoter (Boshart et al., Cell 41 (1995), p 21)

C: an approximately 200 bp fragment isolated from the t-PA cDNA which corresponds to the nucleotide positions 1–199 and which contains the coding region for the signal sequence and the first three amino acids of the mature t-PA (Pennica et al. 1983, Nature 301:214)

D: an approximately 1.5 kb EcoRI fragment which contains a large part of the intron G of the tPA gene (Friezner et al. op.cit., Ny et al. 1984, PNAS 81:5355).

These elements were isolated from the appropriate starting materials and assembled by means of PCR and suitable fusion PCR primers. Subsequently the fused elements were ligated into pBR322 and introduced into *E.coli*. Alternatively the fragments can also be cut out from the respective starting materials and ligated via linkers.

b) Human Cell Line

HeLa was used as the cell line to carry out the endogenous gene activation in which it was shown that the transcription of the t-PA gene can be induced by the addition of phorbol myristate acetate (Waller and Schleuning 1985, J. Biol. Chem. 260:6354). After introduction of the targeting vector by means of electroporation, the cells containing the vector were selected by addition of G418. The cells which, as a result of homologous recombination, secreted a polypeptide with the t-PA domains K2 and P were identified by testing the supernatant of the cells with an ELISA (Imubind-Total tPA, American Diagnostics) which is able to detect the expression of the desired polypeptide.

What is claimed is:

1. A process for the production of muteins of eukaryotic polypeptides wherein
   (i) a nucleic acid molecule capable of homologous recombination is introduced into eukaryotic cells, which contain more than two chromosomes that comprise an endogenous target nucleic acid sequence coding for an endogenous target polypeptide, the nucleic acid molecule comprising
      (a) at least one nucleotide sequence which is homologous to sequences in the coding region of the target nucleic acid sequence and, compared to the endogenous target nucleic acid sequence, has a mutation in the coding region of the target polypeptide and
      (b) a nucleotide sequence coding for a selection marker;
   (ii) the cells are cultured under such conditions that a homologous recombination of the introduced nucleic acid molecule takes place whereby the coding sequence of the endogenous target nucleic acid sequence is mutated by the introduced nucleic acid sequence after the homologous recombination and the mutated endogenous target nucleic acid sequence encodes a mutein of the target polypeptide,
   (iii) the cells in which a homologous recombination has taken place are selected, and
   (iv) the mutein is isolated from the cells, the cell supernatant, or both the cells and cell supernatant, wherein at least part of the mutein is encoded by the endogenous target nucleic acid sequence.

2. The process as claimed in claim 1, wherein
   the cell is a human cell.

3. The process as claimed in claim 2, wherein
   the cell is a HeLa cell, a Namalwa cell or a HT1080 cell.

4. The process as claimed in claim 1, wherein the nucleotide sequence, which is homologous to a nucleotide sequence in the gene locus of the target nucleotide sequence, is in operable linkage with a heterologous expression control sequence.

5. The process as claimed in claim 4, wherein the heterologous expression control sequence is a viral promoter.

6. The process as claimed in claim 1, wherein
   the nucleic acid section coding for the selection marker is a neomycin phosphotransferase gene.

7. The process claimed in claim 1, wherein the nucleic acid molecule introduced into the cell further comprises an amplification gene and wherein the mutated target nucleic acid sequence is amplified after the homologous recombination.

8. The process as claimed in claim 7, wherein said amplification gene is a dihydrofolate reductase gene.

9. The process as claim in claim 1, wherein the target nucleic acid sequence encodes a tissue plasminogen activator (t-PA), erythropoietin, insulin, tumor necrosis factor, interleukin or interleukin receptor.

10. The process as claimed in claim 1, wherein the mutein comprises K2 and P domains of t-PA.

11. Process as claimed in claim 1, wherein
    the mutein is isolated from the supernatant of cells cultured in suspension.

12. The process as claimed in claim 1, wherein
    the mutein is isolated from the supernatant of cells cultured in serum-free medium.

13. A process for the production of a human cell which expresses a mutein of a human target polypeptide comprising,
    (i) introducing a nucleic acid molecule into human cells, which contain more than two chromosomes that comprise an endogenous target nucleic acid sequence coding for an endogenous target polypeptide, the introduced nucleic molecule comprising
       (a) at least one sequence which is homologous to sequences in the coding sequence locus of the endogenous target nucleic acid sequence and, compared to the endogenous target nucleic acid sequence, has a mutation in a coding sequence of a mature form of the endogenous target polypeptide;
       (b) optionally a heterologous expression control sequence for the target nucleic acid sequence, and
       (c) a nucleic acid sequence coding for a selection marker,
    (ii) culturing the cells under such conditions that a homologous recombination of the introduced nucleic acid molecule takes place whereby the coding sequence of the endogenous target nucleic acid sequence is mutated by the introduced nucleic acid molecule after the homologous recombination and the mutated endogenous target nucleic acid sequence encodes a mutein of the target polypeptide, (iii) selecting the cells, in which a homologous recombination has taken place, and (iv) isolating the selected cells, wherein at least part of the mutein is encoded by the endogenous target nucleic acid sequence.

14. The process as claimed in claim 13, wherein the nucleic acid molecule additionally contains an amplification gene and, after the homologous recombination, the mutated target nucleic acid sequence is amplified.

15. The process as claimed in claim 14, wherein said amplification gene is a dihydrofolate reductase gene.

16. A human cell produced by the process as claimed in claim 13 which contains at least one mutated endogenous target nucleic acid sequence which codes for a mutein of a human polypeptide.

17. A method for the production of a mutein of a human polypeptide comprising culturing the human cell of claim 16.

18. The process of claim 5, wherein the viral promoter is a CMV promoter.

* * * * *